United States Patent [19]

Fruchey

[11] Patent Number: 4,485,046
[45] Date of Patent: Nov. 27, 1984

[54] PRODUCTION OF CUPRIC AND MANGANOUS ALKANOATES

[75] Inventor: Olan S. Fruchey, Corpus Christi, Tex.

[73] Assignee: Celanese Corporation, New York, N.Y.

[21] Appl. No.: 426,018

[22] Filed: Sep. 28, 1982

[51] Int. Cl.$^3$ .............................................. C11C 1/00
[52] U.S. Cl. ................................... 260/413; 260/414; 260/429 R; 260/438.1; 562/531
[58] Field of Search ............ 260/413 R, 429 R, 438.1, 260/414; 560/531

[56]  References Cited
U.S. PATENT DOCUMENTS

| | | | |
|---|---|---|---|
| 3,251,646 | 5/1966 | Alon et al. | 260/439 R |
| 3,846,460 | 11/1974 | Fite | 260/439 R X |
| 4,246,185 | 1/1981 | Wood | 260/413 R |
| 4,257,913 | 3/1981 | Fischer | 260/429 R X |
| 4,289,708 | 9/1981 | Scott et al. | 260/413 R |

Primary Examiner—Helen M. S. Sneed
Attorney, Agent, or Firm—L. I. Grim; M. Turken

[57] ABSTRACT

A process for the production of cupric and manganous alkanoates containing from 6 to 9 carbon atoms is described. This process comprises first thermally decomposing a mixture of cupric and manganous oxalates, obtained from the oxidation of $C_6$ to $C_9$ aldehydes to the corresponding acids using a mixture of copper and manganese compounds soluble in the acid product as the catalyst, in the presence of an organic saturated aliphatic monocarboxylic acid containing from 6 to 9 carbon atoms, and in the absence of oxygen, to produce manganous alkanoate and metallic copper. The metallic copper is then oxidized with oxygen to copper in the cupric form, which reacts with the organic saturated aliphatic monocarboxylic acid present to produce cupric alkanoate. The mixtures of cupric and manganous alkanoates obtained can be used as oxidation catalysts, and in fact may be recycled to the reaction sphere in which the $C_6$–$C_9$ saturated aliphatic aldehydes are oxidized to the corresponding monocarboxylic acids for use as catalysts therein.

11 Claims, No Drawings

PRODUCTION OF CUPRIC AND MANGANOUS ALKANOATES

THE INVENTION

This invention relates to a process for producing a mixture of cupric and manganous alkanoates containing from 6 to 9 carbon atoms. These alkanoates can then be used as catalysts for the oxidation of $C_6$ to $C_9$ saturated aliphatic aldehydes to their respective acids. This process involves the initial thermal decomposition of a mixture of cupric and manganous oxalates in the presence of one or more $C_6$–$C_9$ saturated aliphatic monocarboxylic acids and in the absence of oxygen. Manganous alkanoate is immediately produced, together with metallic copper. The copper is then oxidized to the cupric form, which reacts with saturated aliphatic monocarboxylic acid to form cupric alkanoate, thus giving a mixture of cupric and manganous alkanoates which can be separated into its individual constituents or used as such.

BACKGROUND OF THE INVENTION

The overall objective when producing organic saturated aliphatic monocarboxylic acids containing from 6 to 9 carbon atoms by oxidation from their corresponding aldehydes, is to obtain the highest yields and product efficiencies at the highest conversion levels. The use of mixtures of copper and manganese compounds soluble in the acid product as catalysts helps achieve this objective, and is disclosed in copending U.S. patent application Ser. No. 345,890, filed on Feb. 4, 1982 in the names of Hobbs, Jr. and Thigpen and assigned to Celanese Corporation. However, copper has a tendency to plate out in the distillation apparatus used for acid product recovery, resulting in undesirable mechanical problems such as erosion of reboilers and pump impellers and rapid pump seal failures.

A method of overcoming this copper plating problem, involving adding oxalic acid to the acid product to precipitate copper and manganese as the oxalates, then filtering the oxalates from the acid product prior to the acid distillation step, is described in U.S. Pat. No. 4,289,708, issued Sept. 15, 1981 to Scott et al and assigned to Celanese Corporation. Copper and manganese can also be separated from the acid product, again as the oxalates, by adding aqueous oxalic acid to precipitate manganese and copper oxalates into the aqueous phase, which is then separated from the acid product by decantation of the acid. The acid can then be further purified by distillation. This latter process is described in U.S. Pat. No. 4,246,185, issued Jan. 12, 1981 to Wood, Jr. and assigned to Celanese Corporation.

The foregoing separation processes result in the production of substantial amounts of cupric and manganous oxalates. It is the purpose of this invention to convert these oxalates to alkanoates useful as catalysts for recycle in the oxidation of $C_6$–$C_9$ saturated aliphatic aldehydes to the corresponding monocarboxylic acid.

U.S. Pat. No. 3,133,942, issued May 19, 1964 to Hahl and assigned to Badische Anilin- & Soda-Fabrik Aktiengesellschaft, describes a technique for the production of metal salts, including copper salts of organic acids, including saturated aliphatic monocarbolic acids having 1 to 8 carbon atoms, oleic acid and benzoic acid, which involves reacting the metal with the acid in the presence of free oxygen. The reactions of n-butyric, n-valeric and n-caprylic acids with copper powder in the presence of oxygen to produce copper (II) butyrate, copper (II) valerate and copper (II) caprylate, respectively, are specifically disclosed. Hahl makes no mention, however, of conducting such reactions in the presence of manganese compounds such as manganese alkanoate and the products obtained by the thermal decomposition of manganous oxalate and cuprous oxalate in the presence of a $C_6$–$C_9$ saturated aliphatic monocarboxylic acid. In particular, Hahl has no teaching of the conversion of the oxalates suspended in an alkanoic acid to form metallic copper and manganese alkanoate directly. Finally, Hahl's teaching does not include the treatment of manganese in any form whatever to obtain a manganese alkanoate since the normal potential of manganese is $-1.029$ volt and thus does not fall within the range of the normal potential of $-0.80$ and $+0.5$ volt described by Hahl.

DETAILED DESCRIPTION OF THE INVENTION

The mixture of manganous and cupric oxalates utilized as the starting material for the process of the present invention is first combined with one or more organic saturated aliphatic monocarboxylic acids containing from 6 to 9 carbon atoms, such as hexanoic acid, heptanoic acid, nonanoic acid, and the like. The resulting mixture of oxalates and free acids is then subjected to thermal decomposition conditions, which essentially involve reaction at temperatures in the range from about 225° C. to about 300° C., preferably from about 225° C. to about 275° C., in an atmosphere substantially free of oxygen, for a sufficient period of time to yield manganous oxide and metallic copper as well as carbon monoxide, carbon dioxide and water. Oxygen is excluded from the decomposition reaction to avoid further oxidation of the organic acids present. Manganous oxide readily reacts with the $C_6$–$C_9$ acid or acids present to form the corresponding manganous alkanoates having $C_3$–$C_9$ carbon atoms. Metallic copper, however, does not react with these acids under these conditions.

The solution containing manganous alkanoate, acid and metallic copper is cooled to a temperature at which metallic copper can be oxidized to the cupric form, but at which the acid will not oxidize. Such temperatures range from about 50° C. to about 125° C., and preferably from about 80° C. to about 110° C. The cooled solution is then contacted with oxygen, in the form of air at a pressure maintained from about 200 to about 300 psig, preferably from about 225 to about 275 psig, for a period of time sufficient to convert the metallic copper to the cupric form. Ordinarily, this will take from about ½ to aout 10 hours, and preferably from about 1 to about 6 hours. The cupric ions produced by oxidation of metallic copper immediately react with available organic acid to produce the corresponding cupric alkanoate containing 6 to 9 carbon atoms. Thus, for example, if heptanoic acid was used as the acid in which cupric oxalate and manganous oxalate were thermally decomposed, manganous heptanoate and eventually cupric heptanoate would be produced. The resulting mixture of cupric and manganous alkanoates, e.g., cupric and manganous heptanoate, can be used as the catalyst for the oxidation of heptanal to heptanoic acid.

The invention will be illustrated by the following example.

EXAMPLE

In a stirred 300 cc stainless steel autoclave, 100 milliliters of heptanoic acid and 10 milliliters of a slurry containing 60 weight percent water and 40 weight percent of a mixture of cupric and manganous oxalates (equal weights of each oxalate) were heated to 250° C. for 4 hours at autogenous pressures. This resulted in a mixture containing heptanoic acid, manganous heptanoate and finely divided elemental copper. This mixture was cooled to 100° C., then pressured with air at 250 psig and stirred for 6 hours. During this time, all of the finely divided copper was oxidized to the cupric form which immediately reacted with heptanoic acid to form cupric heptanoate. The resulting solution, containing 1 weight percent each of cupric heptanoate and manganous heptanoate in heptanoic acid, is suitable as the oxidation catalyst to produce heptanoic acid from heptanal using the same process described in the above-mentioned copending U.S. patent application, Ser. No. 345,890. These catalysts can be recycled to the catalytic heptanal oxidation process for reuse.

What is claimed is:

1. A process for producing a mixture of cupric and manganous alkanoates containing from 6 to 9 carbon atoms comprising (1) thermally decomposing a mixture of cupric oxalate and manganous oxalate in the presence of an organic saturated aliphatic monocarboxylic acid containing from 6 to 9 carbon atoms in the absence of oxygen, producing the corresponding manganous alkanoate in admixture with metallic copper, (2) oxidizing said metallic copper to the cupric form in the presence of oxygen, and (3) reacting said copper in the cupric form with said acid to produce the corresponding cupric alkanoate.

2. The process of claim 1 wherein the organic saturated aliphatic monocarboxylic acid is heptanoic acid.

3. The process of claim 1 wherein the organic saturated aliphatic monocarboxylic acid is nonanoic acid.

4. The process of claim 1 wherein the thermal composition of the cupric and manganous oxalates is carried out at temperatures ranging from about 220° C. to about 300° C.

5. The process of claim 1 wherein the oxidation of the metallic copper is conducted at air pressures ranging from about 100 to about 500 psig.

6. The process of claim 1 wherein the oxidation of the metallic copper is conducted at air pressures ranging from about 225 to about 275 psig at temperatures ranging from about 50° C. to about 125° C.

7. A process for producing a mixture of cupric and manganous heptanoates comprising (1) thermally decomposing a mixture of cupric and manganous oxalates at a temperature of from about 225° C. to about 275° C. in the presence of heptanoic acid and the absence of oxygen to produce manganous heptanoate and metallic copper, (2) oxidizing said metallic copper to the cupric form with air at a temperature of from about 80° C. to about 110° C. and an air pressure of from about 225 to about 275 psig, and (3) reacting said copper in the cupric form with said heptanoic acid to form cupric heptanoate.

8. A process for producing a mixture of cupric and manganous nonanoates comprising (1) thermally decomposing a mixture of cupric and manganous oxalates at a temperature of from about 250° C. to about 275° C. in the presence of nonanoic acid and the absence of oxygen to produce manganous nonanoate and metallic copper, (2) oxidizing said metallic copper to the cupric form with air at a temperature of from about 80° C. to about 110° C. and an air pressure of from about 225 to about 275 psig, and (3) reacting said copper in the cupric form with said nonanoic acid to form cupric nonanoate.

9. In a process for the production of a saturated aliphatic monocarboxylic acid containing from 6 to 9 carbon atoms by oxidation of its corresponding aldehyde using a mixture of cupric and manganous compounds as oxidation catalyst wherein the cupric and manganous compounds in the product mixture are reacted with oxalic acid to form cupric and manganous oxalates and said oxalates are separated from said saturated aliphatic monocarboxylic acid, the improvement comprising thermally decomposing said oxalates in the presence of an organic saturated aliphatic monocarboxylic acid containing from 6 to 9 carbon atoms in the absence of oxygen, producing the corresponding manganous alkanoate and metallic copper; oxidizing said metallic copper to the cupric form in the presence of oxygen; reacting said copper in the cupric form with said acid to produce the corresponding cupric alkanoate, and recycling said manganous and cupric alkanoates to the oxidation reaction wherein a saturated aliphatic monocarboxylic acid containing 6 to 9 carbon atoms is produced from its corresponding aldehyde.

10. The process of claim 9 wherein heptanal is oxidized to heptanoic acid and the manganous and cupric alkanoates formed are manganous heptanoate and cupric heptanoate.

11. The process of claim 9 wherein nonanal is oxidized to nonanoic acid and the manganous and cupric alkanoates formed are manganous nonanoate and cupric nonanoate.

* * * * *